(12) United States Patent
Dye et al.

(10) Patent No.: US 9,820,860 B2
(45) Date of Patent: Nov. 21, 2017

(54) REMOVABLE HEAD ASSEMBLY FOR ARTIFICIAL JOINT

(71) Applicant: Zimmer, Inc., Warsaw, IN (US)

(72) Inventors: Donald W. Dye, Warsaw, IN (US); Steven Humphrey, Warsaw, IN (US)

(73) Assignee: ZIMMER, INC., Warsaw, IN (US)

( * ) Notice: Subject to any disclaimer, the term of this patent is extended or adjusted under 35 U.S.C. 154(b) by 6 days.

(21) Appl. No.: 14/955,128

(22) Filed: Dec. 1, 2015

(65) Prior Publication Data

US 2016/0166390 A1 Jun. 16, 2016

Related U.S. Application Data

(60) Provisional application No. 62/089,985, filed on Dec. 10, 2014.

(51) Int. Cl.
*A61F 2/36* (2006.01)
*A61F 2/40* (2006.01)
(Continued)

(52) U.S. Cl.
CPC .......... *A61F 2/4014* (2013.01); *A61F 2/3609* (2013.01); *A61F 2/4637* (2013.01); *A61B 17/1664* (2013.01); *A61B 17/8841* (2013.01); *A61F 2/4607* (2013.01); *A61F 2/4612* (2013.01); *A61F 2/4684* (2013.01); *A61F 2002/2828* (2013.01); *A61F 2002/30004* (2013.01); *A61F 2002/30245* (2013.01); *A61F 2002/30247* (2013.01); *A61F 2002/30331* (2013.01); *A61F 2002/30332* (2013.01); *A61F 2002/30561* (2013.01); *A61F 2002/30649* (2013.01); *A61F 2002/30652* (2013.01); *A61F 2002/30672* (2013.01);
(Continued)

(58) Field of Classification Search
CPC ............ A61F 2002/30649–2002/30652; A61F 2/36–2002/4096
See application file for complete search history.

(56) References Cited

U.S. PATENT DOCUMENTS 5,156,626 A * 10/1992 Broderick ............. A61F 2/4609
623/22.12
2003/0229357 A1* 12/2003 Dye ...................... A61F 2/4637
606/99

(Continued)

*Primary Examiner* — Yashita Sharma
*Assistant Examiner* — Rebecca Preston
(74) *Attorney, Agent, or Firm* — Schwegman Lundberg & Woessner, P.A.

(57) ABSTRACT

In an artificial joint that includes a head assembly attached by taper fit to a proximal portion of a surgically implanted stem, it may become necessary to surgically remove the head assembly. A puller can simultaneously apply a force distally to a non-peripheral portion of a proximal side of the head assembly and proximally to several locations spaced apart around a circumference of the distal side of the head assembly. In some examples, the proximal side of the head assembly includes a plug disposed at the non-peripheral portion. The puller can force the plug into contact with the proximal end of the stem, then apply the distal force through the plug to the stem. In other examples lacking a plug, the non-peripheral portion of the head can deform or break in response to the applied distal force, so that the distal force can apply to the stem.

9 Claims, 11 Drawing Sheets

(51) Int. Cl.
*A61F 2/30* (2006.01)
*A61F 2/28* (2006.01)
*A61F 2/46* (2006.01)
*A61B 17/16* (2006.01)
*A61B 17/88* (2006.01)

(52) U.S. Cl.
CPC ............... *A61F 2002/30925* (2013.01); *A61F 2002/365* (2013.01); *A61F 2002/3611* (2013.01); *A61F 2002/3621* (2013.01); *A61F 2002/4018* (2013.01); *A61F 2002/4037* (2013.01); *A61F 2002/4641* (2013.01); *A61F 2240/001* (2013.01)

(56) References Cited

U.S. PATENT DOCUMENTS

| | | |
|---|---|---|
| 2005/0143829 A1 | 6/2005 | Ondrla et al. |
| 2013/0253659 A1 | 9/2013 | Klotz et al. |

\* cited by examiner

REMOVABLE HEAD ASSEMBLY FOR ARTIFICIAL JOINT

CROSS-REFERENCE TO RELATED APPLICATION

This application claims the benefit of U.S. Provisional Application No. 62/089,985, filed Dec. 10, 2014, and titled "REMOVABLE HEAD ASSEMBLY FOR ARTIFICIAL JOINT", which is incorporated by reference in its entirety herein.

BACKGROUND

A surgically implanted artificial joint can require surgical revision or alteration, in order to treat conditions such as infection, disassociation, or implant fracture. There is ongoing effort to develop artificial joints and removal procedures that reduce trauma to the joint, the bone and surrounding soft tissue.

OVERVIEW

A multi-element artificial joint can include a stem, which can be surgically implanted within a bone of the patient. The stem can have a distal portion, which can be implanted into the bone, and a proximal portion opposite the distal portion. The multi-element artificial joint can further include a head assembly, which can attach to the proximal portion of the stem.

In some examples, the head assembly can attach to the stem with a taper fit, such as a Morse taper fit or other suitable taper fit. To achieve the taper fit, the head assembly and stem have corresponding mating surfaces that are slightly conical. When the head assembly and stem are forced against each other, the mating surfaces elastically deform the head assembly and the stem at the taper interface. The elastic deformation locks the head assembly to the stem.

To remove the head assembly from the stem, a practitioner can use a puller, such as a gear puller, to simultaneously apply several forces onto various locations on the head assembly and stem. For instance, the puller can push on a proximal end of the stem and simultaneously pull on the head at several locations around the periphery of the head. The puller can increase these pushing and pulling forces until the head detaches from the stem.

Using a puller to remove the head assembly from the stem has several advantages. For example, the forces involved with the head assembly removal are localized in the vicinity of the head assembly, and do not extend to the distal end of the stem or the bone into which the stem is implanted. Compared with a head assembly removal procedure that involves hammering against the stem, using the puller as described can reduce trauma to the bone or soft tissue surrounding the bone and implanted stem, which is desirable.

This Overview is intended to provide examples of the present patent document. It is not intended to provide an exclusive or exhaustive explanation of the invention. The Detailed Description below is included to provide further information about the present adjustable reaming device.

BRIEF DESCRIPTION OF THE DRAWINGS

In the drawings, which are not necessarily drawn to scale, like numerals describe similar components in different views. The drawings illustrate generally, by way of example, but not by way of limitation, various embodiments discussed in the present patent document.

DETAILED DESCRIPTION

Figure 1:
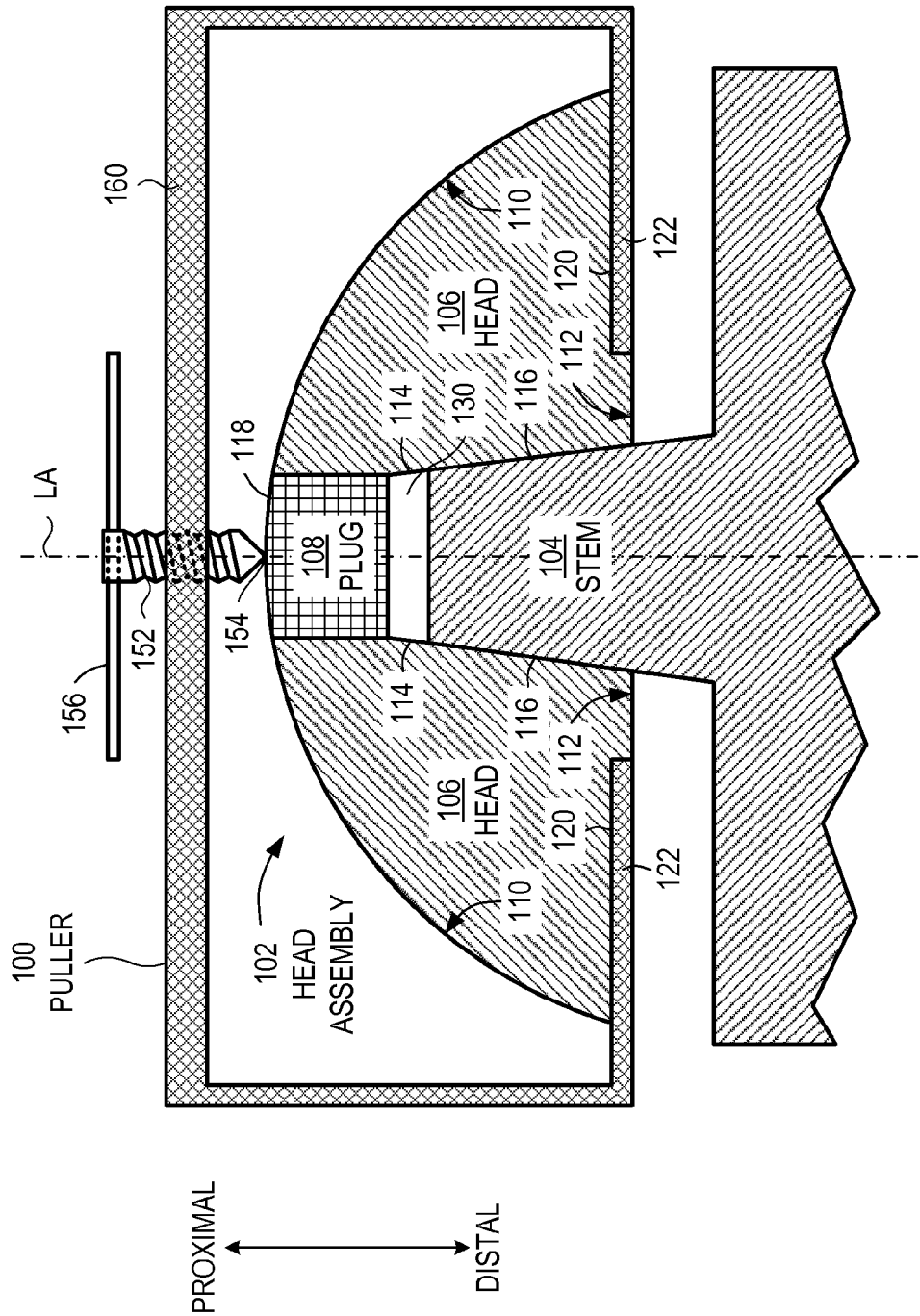
FIG. 1 shows a side-view cross-section of an example of a proximal portion of an artificial joint.

FIG. 1 shows a side-view cross-section of an example of a proximal portion of an artificial joint. The artificial joint of FIG. 1, and of subsequent figures, is suitable for use in a shoulder or hip of a human or animal, and can have other suitable uses as well. The artificial joint can include a head assembly 102 and a stem 104, which can be joined together with a taper fit and remain joined inside a patient's body during the time that the artificial joint is in use. In a surgical procedure to remove a portion of the artificial joint, a practitioner can use a puller 100, such as a gear puller, to remove the head assembly 102 from the stem 104. The puller 100 is not part of the artificial joint.

In the example of FIG. 1, the head assembly 102 includes a head 106 and a plug 108.

The head 106 can have a proximal side 110. The proximal side 110 can be convex, spherical, and/or dome-shaped. In some examples, the proximal side 110 can be matched to a particular anatomical feature, which can vary in size or shape from patient to patient, or from joint to joint. For instance, the proximal side 110 of a head 106 for a shoulder joint can be shaped differently from a proximal side 110 of a head 106 for a hip joint. Other suitable shapes can also be used.

The head 106 can have a distal side 112 opposite the proximal side 110. In some examples, the distal side 112 can be flat. In some examples, the distal side 112 can be parallel to a corresponding structure on the stem 104. In some examples, the distal side 112 can contact the corresponding structure on the stem 104.

The head 106 can have an internal wall 114 that defines an aperture 130 extending from the proximal side 110 to the distal side 112. The internal wall 114 can have a distal portion 116 shaped to form a taper fit with a proximal portion of the stem 104.

The plug 108 can be disposed in a proximal portion of the aperture 130. The plug 108 can have a proximal side 118 flush with the proximal side 110 of the head 106. In some examples, the proximal side 118 of the plug 108 can form a continuous articular surface with the proximal side 110 of the head 106. In some examples, the plug 108 can be disposed in a non-peripheral portion of the proximal side of the head assembly 102. In some examples, the internal wall 114 can have a proximal portion shaped so that the plug 108 can be forced distally into the aperture 130. For instance, the proximal portion of the internal wall 114 can be parallel to a longitudinal axis (LA) of the head 106. In some examples, the proximal portion of the internal wall 114 can be cylindrical. In other examples, the proximal portion of the internal wall 114 can be tapered inward, either with the same taper as the distal portion 116 or with a different taper.

The distal side 112 can include a plurality of recessed portions 120 thereon (shown more clearly in the examples of FIGS. 4, 5, 8, and 9). The recessed portions 120 can be disposed at peripheral locations that are spaced apart around a circumference of the distal side 112. The recessed portions 120 can prevent respective arms 122 of the puller 100 from slipping out of position during a removal procedure. In some examples, the recessed portions 120 are recessed by an amount greater than or equal to a thickness of an arm 122 of the puller 100. In some examples, the recessed portions 120 can extend to an outer edge of the distal side 112 of the head 106, which can allow insertion of a puller arm 122 into the recessed portion 120, if the head 106 and stem 104 are in contact or are closely spaced. In some examples, the distal side 112 of the head 106 can include two diametrically-opposed recessed portions 120 thereon. Using just two recessed portions 120 can ensure that a practitioner positions the arms of the puller 100 at specified locations on the distal side 112 of the head 106. Positioning the two recessed portions 120 diametrically opposed to each other can reduce torque applied to the head 106 during a removal procedure, compared with other locations.

To remove the head assembly 102 from the stem 104, a practitioner can use puller 100 to simultaneously apply several forces onto various locations on the head assembly 102 and stem 104. Puller 100 can include a screw 152 having a distal end 154, where the distal end 154 applies a distal force to the plug 108. Puller 100 can include a plurality of arms 122, which apply proximal force to respective recessed portions 120 of the head 106. A practitioner can rotate a T-handle 156 coupled to the screw, which in turn can rotate the screw 152 with respect to the arms 122. In some examples, the practitioner can hold a body 160 of the puller 100 while rotating the T-handle, to help avoid generating large torques that can be translated along the stem 104 to the bone.

The puller 100 can simultaneously apply balanced proximal and distal forces to the head assembly 102, which can sum to zero, so that no net forces are transmitted along the length of the stem 104 to the bone. For instance, if the puller 100 includes two arms 122, then the distal force applied by the distal end 154 of the screw 152 is twice the proximal force applied by each arm 122. As a specific example at a particular instant in time, if each arm 122 applies a proximal force of 1250 N, then the distal end 154 of the screw 152 applies a distal force of 2500 N. Likewise, if the puller 100 includes four arms 122, then the distal force applied by the distal end 154 of the screw 152 is four times the proximal force applied by each arm 122.

During a first stage of a removal procedure, the practitioner adjusts the puller 100 to bring the puller 100 into contact with respective portions of the head assembly 102. The puller 100 experiences no resistance at the first stage. The practitioner freely rotates the T-handle 156 to adjust the longitudinal separation between the distal end 154 of the screw 152 and the arms 122. This first stage ends when the distal end 154 of the screw 152 contacts the plug 108, and the arms 122 contact respective recessed portions 120 of the head 106.

In a second stage of the removal procedure, the practitioner adjusts the puller 100 to push the plug 108 into contact with the stem 104. Once the puller 100 is properly positioned from the first stage, the practitioner rotates the T-handle 156, which decreases the longitudinal separation between the screw 152 and the arms 122. Rotation of the T-handle 156 forces the distal end 154 of the screw 152 against the plug 108, thereby pushing the plug 108 distally into the aperture 130. This second stage ends when the plug 108 contacts the proximal end of the stem 104.

In a third stage of the removal procedure, the practitioner adjusts the puller 100 to force the head 106 against the stem 104. The practitioner applies a torque to the T-handle 156. The puller 100 converts the torque into a distal force, which is transmitted through the distal end 154 of the screw 152, and through the plug 108, to the proximal end of the stem 104. The puller 100 exerts proximal forces, through the arms 122, to respective recessed portions 120 of the head 106. The proximal and distal forces cancel, so that no net forces are transmitted along the length of the stem 104 to the bone. The practitioner increases the applied torque on the T-handle 156 until the press fit yields between the stem 104 and the head 106. When the press fit yields, the head assembly 102 detaches from the stem 104.

In a fourth stage of the removal procedure, the practitioner removes the detached head assembly 102 and the puller from the stem 104. The practitioner can then replace the head assembly as needed.

It will be understood that the puller 100 is but one example of a puller that can controllably and simultaneously apply balanced proximal and distal forces to the plug 108 and head assembly 102, and that other puller configurations can also be used. For instance, another example can include one or more geared levers, rather than a screw, to increase the applied proximal and distal forces.

In some examples, such as the example of FIG. 1, the plug 108 and aperture 130 are centered, with respect to the longitudinal axis (LA) of the head 106. In some examples, this centered geometry can be suitable for an artificial hip joint, where the centered head 106 can be a femoral head.

Figure 2:
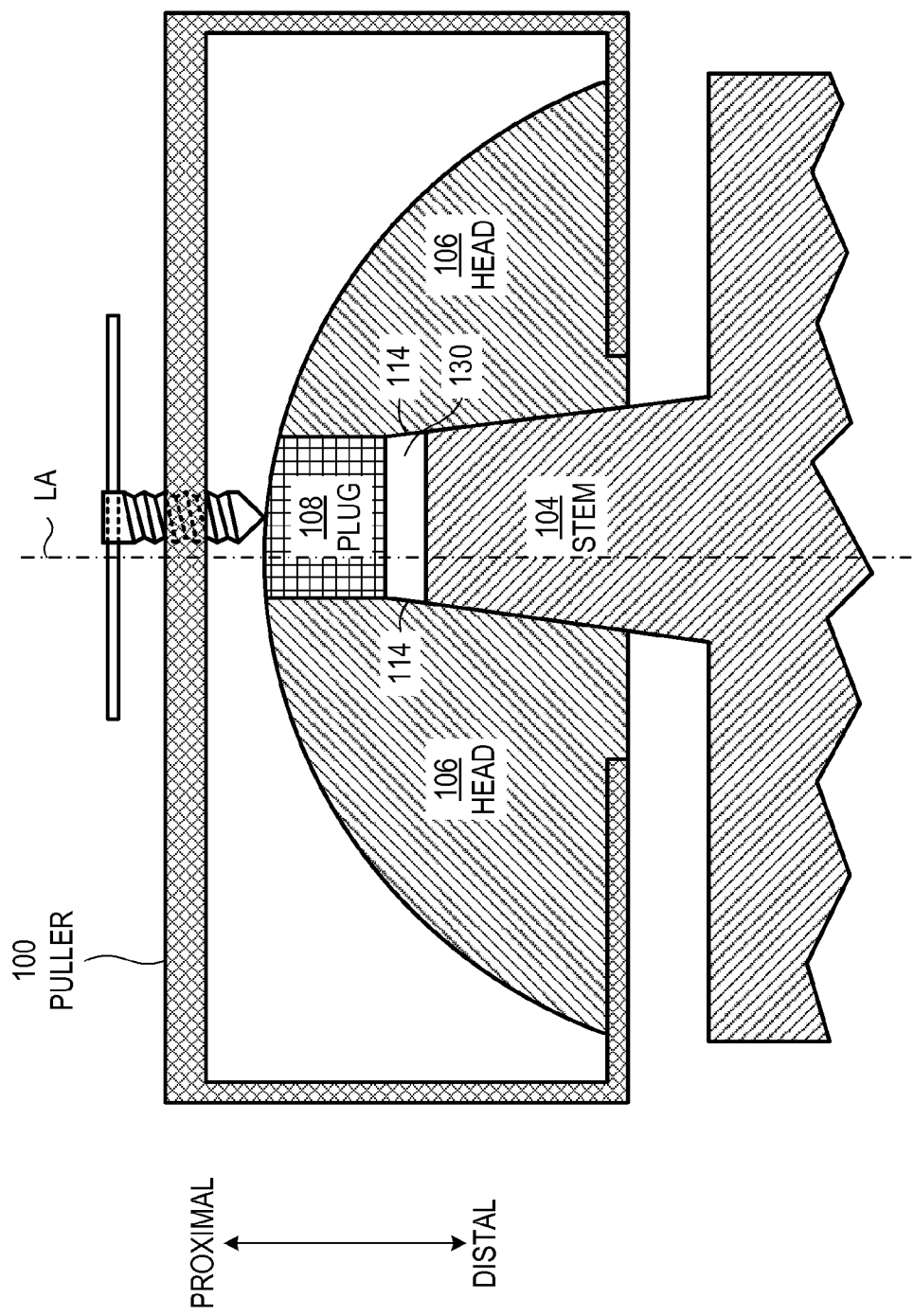
FIG. 2 shows an example of a proximal portion of an artificial joint, in which the plug and aperture are decentered, with respect to a longitudinal axis of the head.

FIG. 2 shows an example of a proximal portion of an artificial joint, in which the plug 108 and aperture 130 defined by the internal wall 114 are decentered, with respect to the longitudinal axis (LA) of the head 106. In some examples, the plug 108 can be disposed in a non-peripheral portion of the proximal side of the head assembly 102, even if decentered. For instance, the longitudinal axis (LA) of the head 106 can intersect the plug 108 and the aperture 130. In some examples, this decentered, or eccentric, geometry can be suitable for an artificial shoulder, where the decentered, or eccentric, head can be a humeral head.

Figure 3:
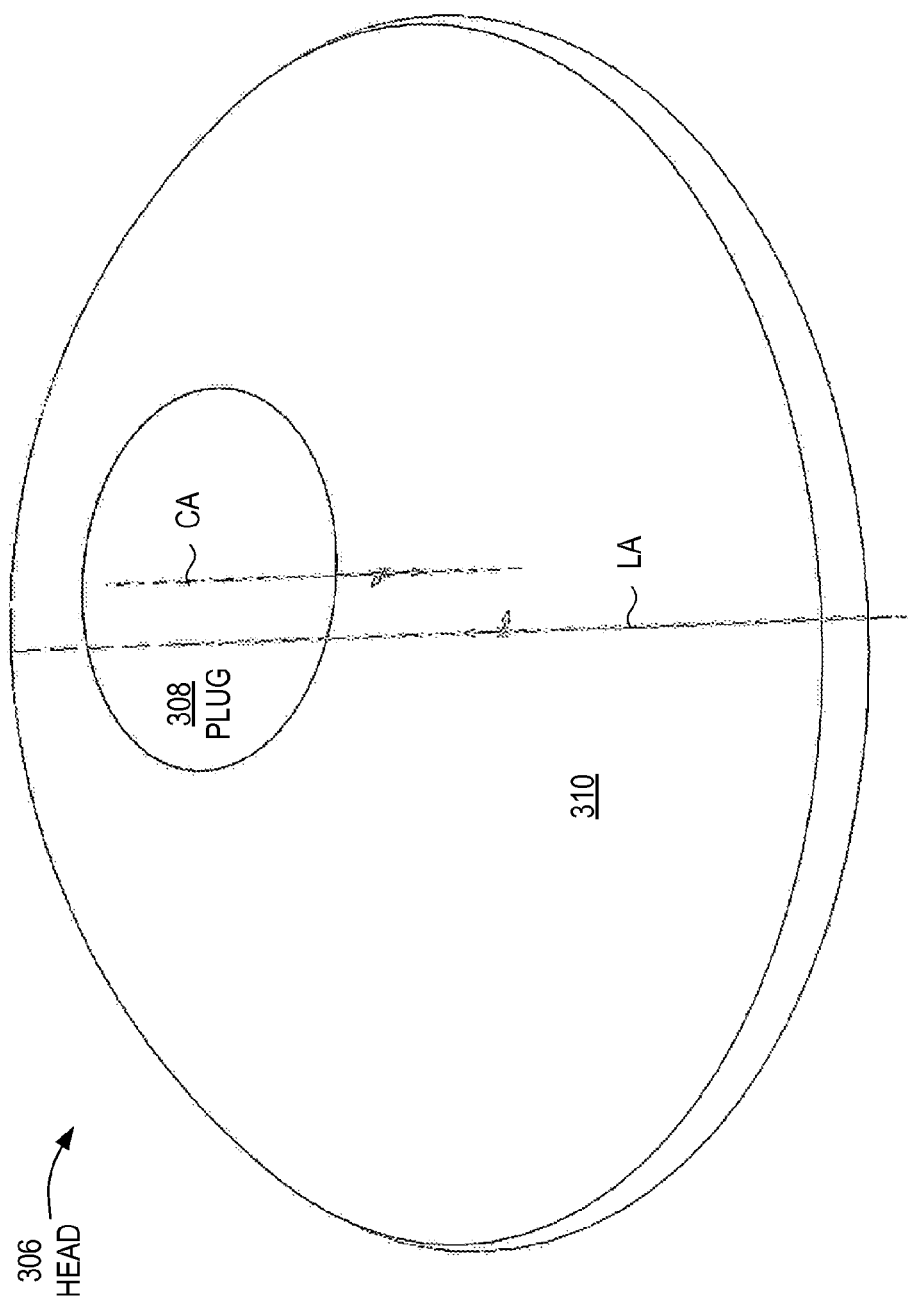
FIGS. 3, 4, and 5 show the proximal side, the distal side and a side view of another example of a head and plug.
Figure 4:
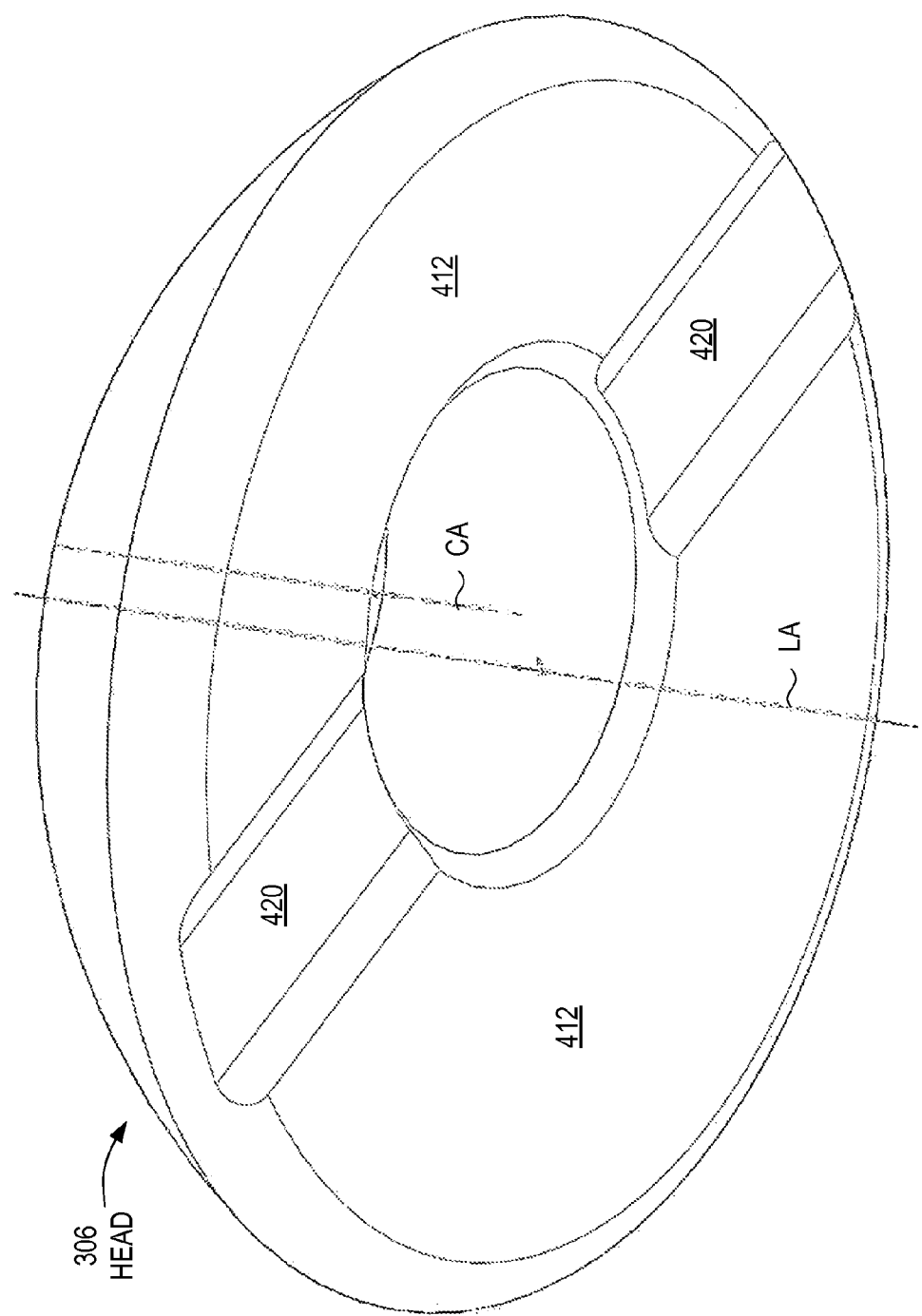
Figure 5:
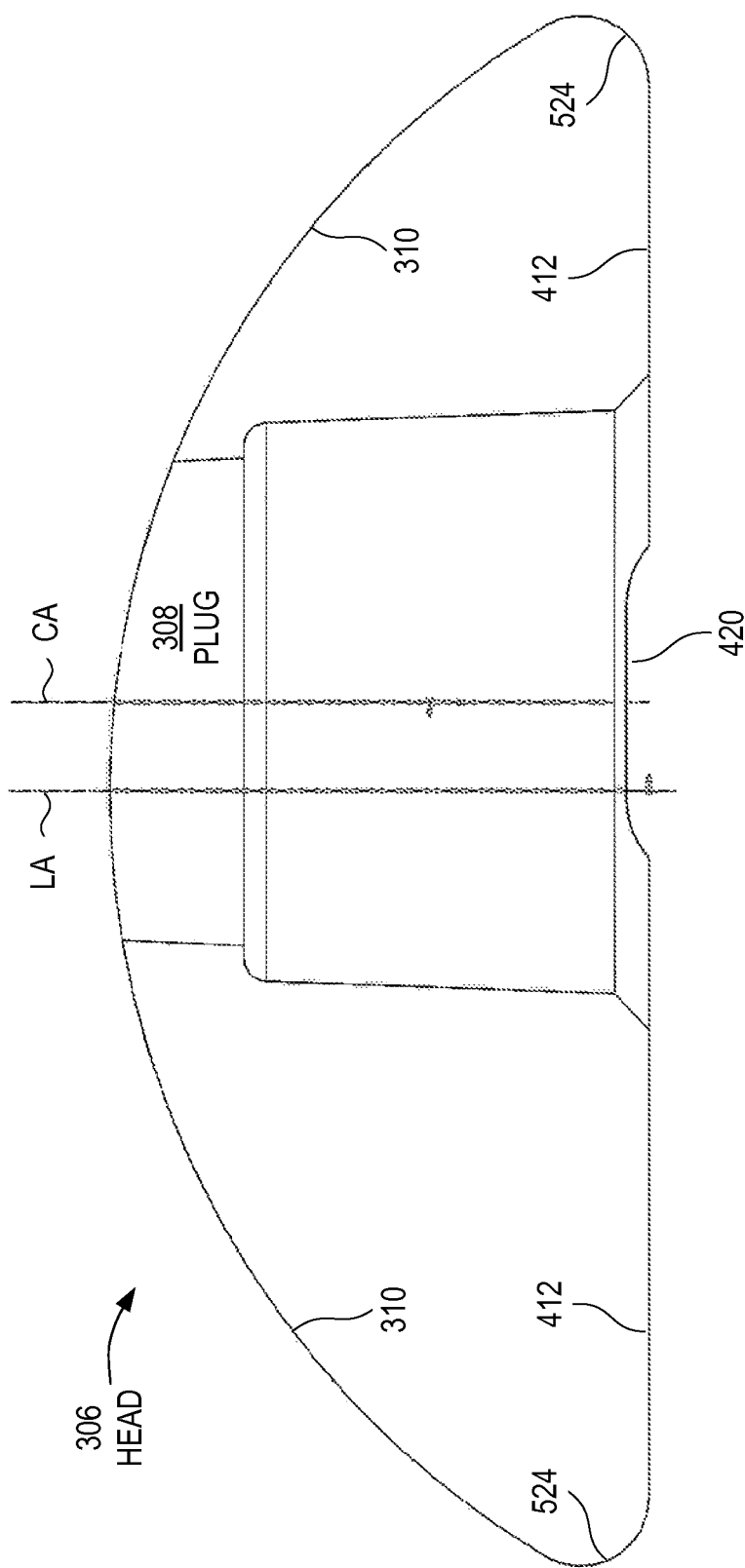

FIGS. 3, 4, and 5 show the proximal side 310, the distal side 412 and a side view of another example of a head 306 and plug 308. A central axis (CA) of the plug 308 is displaced laterally, with respect to the longitudinal axis (LA) of the head 306. In some examples, the proximal side 310 of the head 306 can join the distal side 412 of the head at a curved region 524, which can help reduce a number of sharp edges on the artificial joint.

The recessed portions 420 are more clearly visible in FIGS. 4 and 5 than the recessed portions 120 in FIGS. 1 and 2. Compared with the example of FIG. 2, the recessed portions 420 in FIGS. 4 and 5 are oriented perpendicularly to those in FIG. 2, when viewed from the distal end of the head. Other orientations for the recessed portions 420 can also be used.

Figure 6:
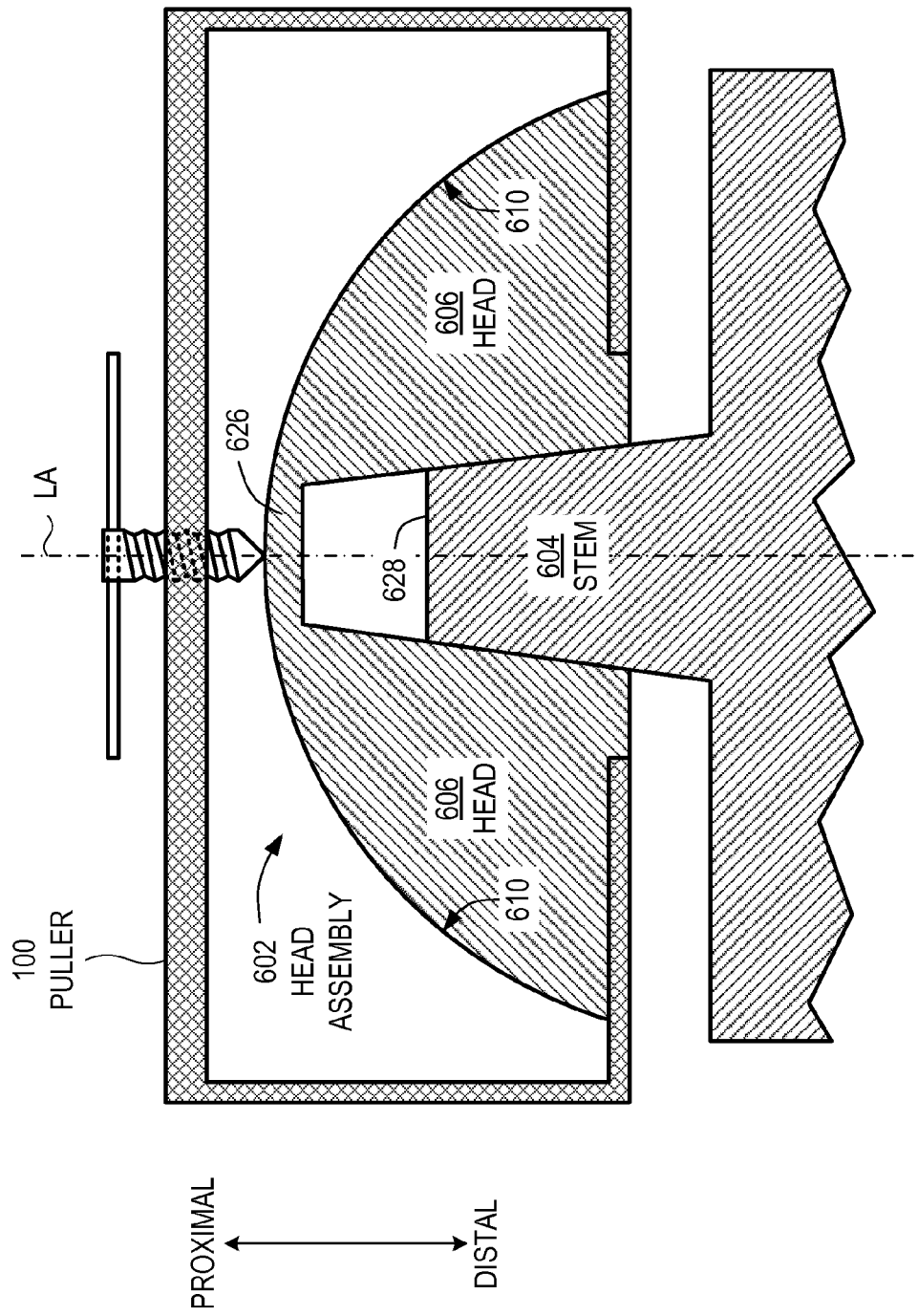
FIG. 6 shows a side-view cross-section of another example of a proximal portion of an artificial joint.

FIG. 6 shows a side-view cross-section of another example of a proximal portion of an artificial joint. Compared with the examples of FIGS. 1-5, the head assembly 602 of FIG. 6 lacks a plug extending through the proximal side, and instead includes a head 606 with a proximal side 610 that has a reduced thickness in a non-peripheral portion 626. In some examples, the non-peripheral portion 626 can be located proximal to a distal end 628 of the stem 104. In the example of FIG. 6, the non-peripheral portion 626 is centered on the longitudinal axis (LA) of the head. In other examples, the non-peripheral portion 626 can be decentered, with respect to the longitudinal axis (LA). In some of these examples, the longitudinal axis (LA) can intersect the non-peripheral portion 626.

Figure 7:
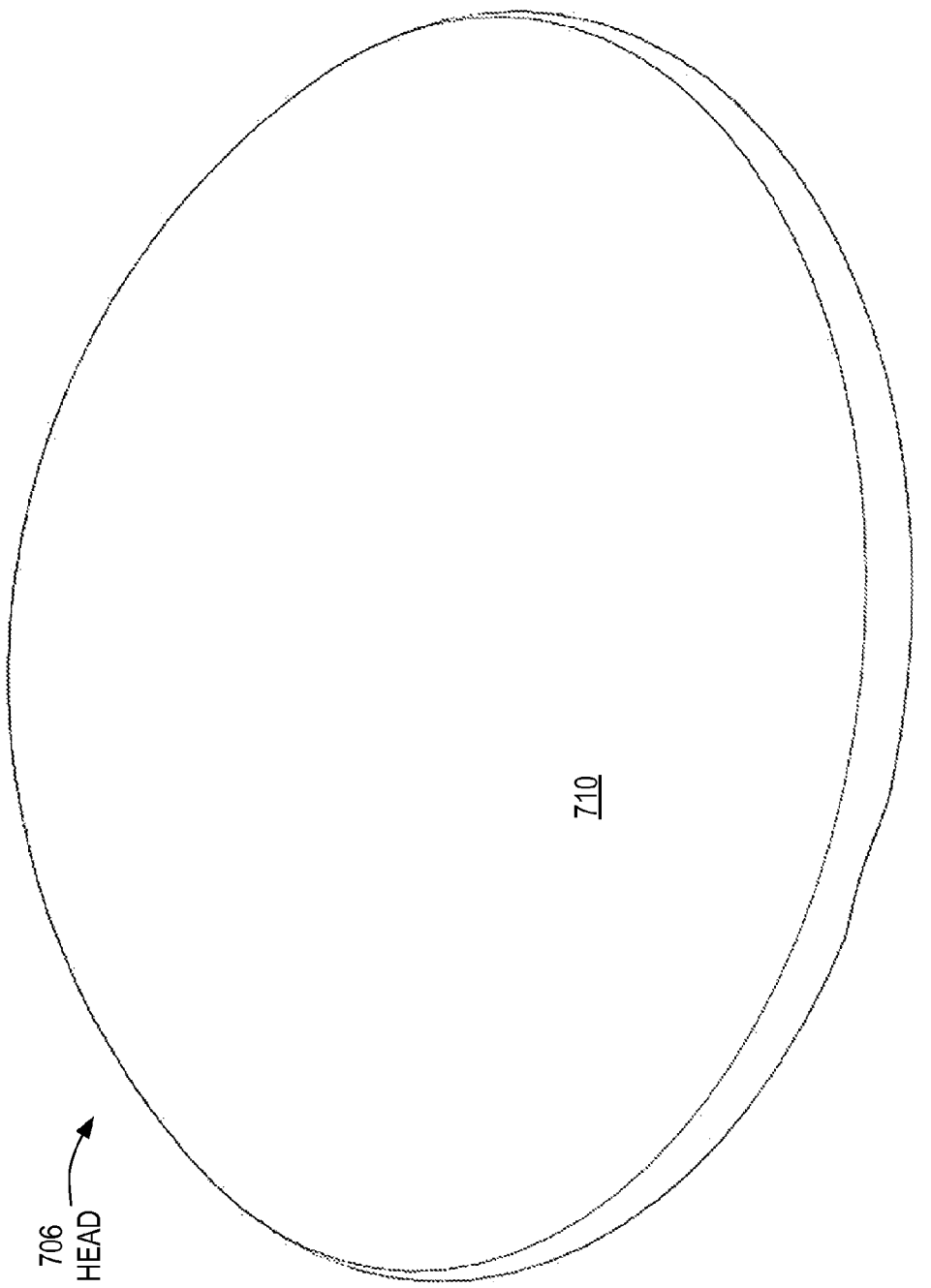
FIGS. 7, 8, and 9 show the proximal side, the distal side, and a cutaway side view of another example of a head having a reduced thickness in a non-peripheral portion.
Figure 8:
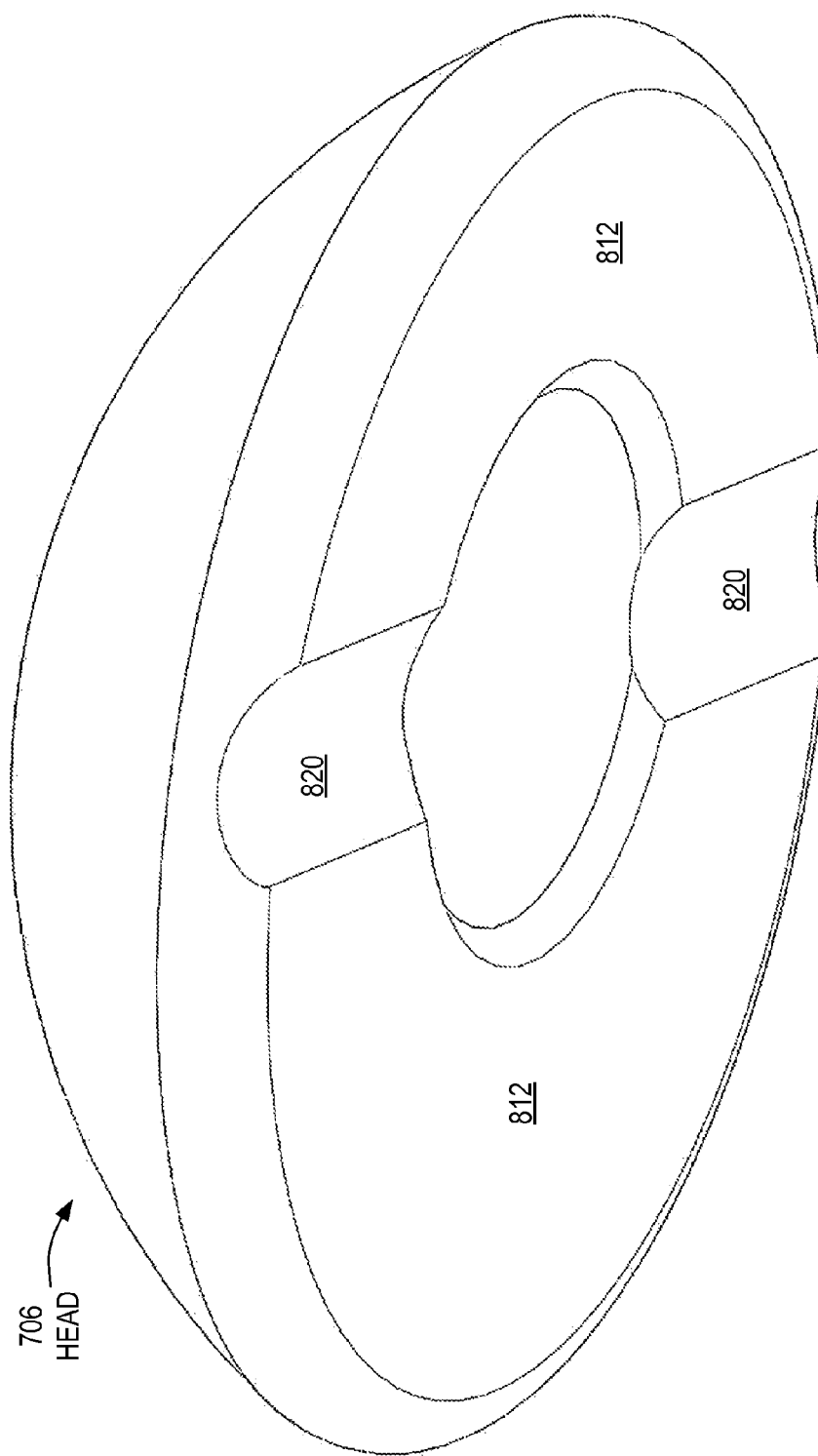
Figure 9:
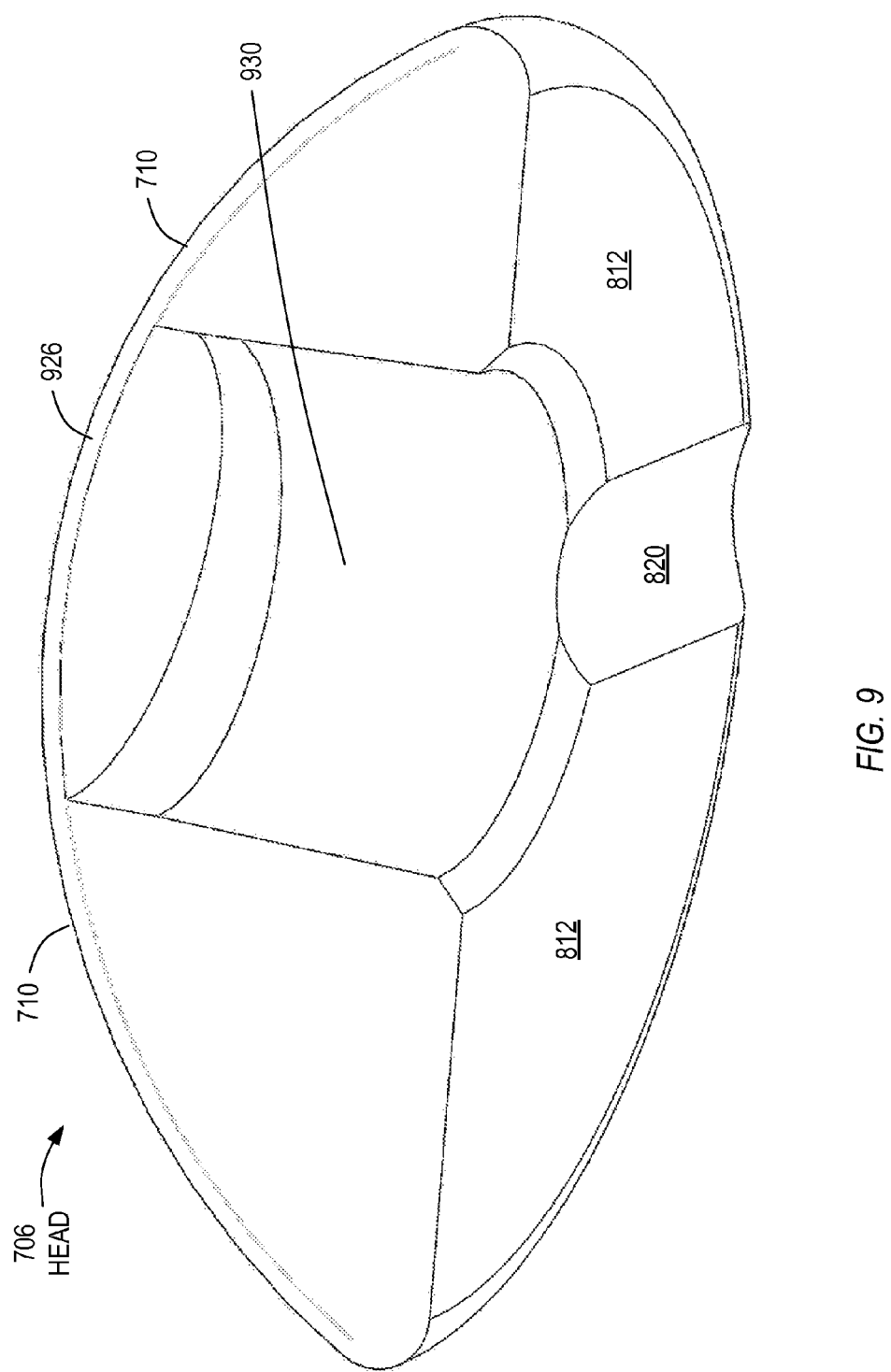

FIGS. 7, 8, and 9 show the proximal side 710, the distal side 812, and a cutaway side view of another example of a head having a reduced thickness in a non-peripheral portion 926, rather than including a plug. Compared with the example of FIG. 6, the aperture 930 is decentered with respect to a longitudinal axis (LA) of the head. In the views of FIGS. 8 and 9, the aperture 930 is translated to the right, with respect to the center of the head.

In addition, the recessed portions 820 of FIGS. 7-9 have rounded centers, while the recessed portions 420 of FIGS. 4 and 5 include flat centers. It will be understood that either shape can be used for any of the recessed portions discussed herein.

Figure 10:
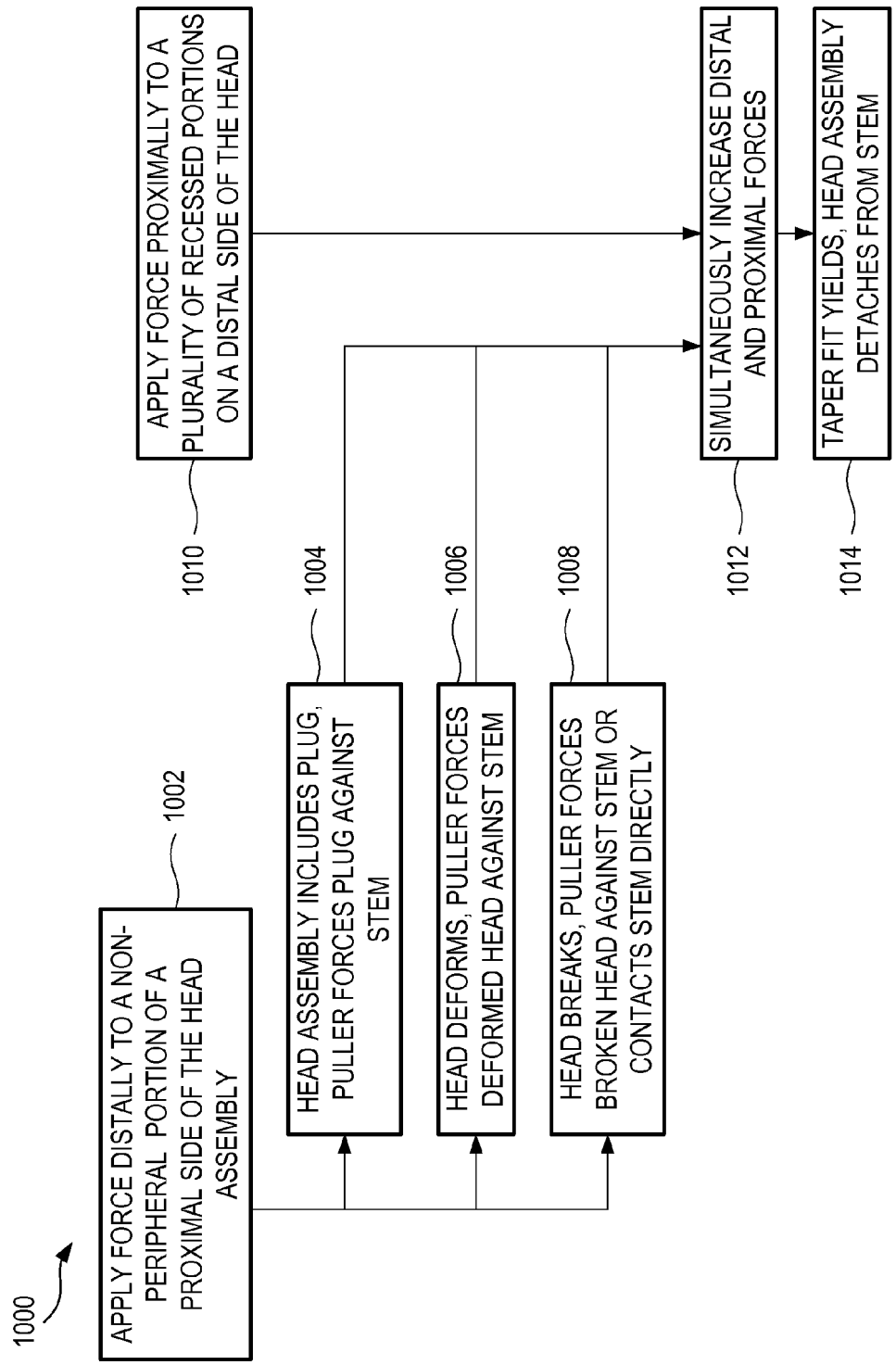
FIG. 10 is a flow chart of an example of a method for removing a head assembly from a surgically implanted stem.

FIG. 10 is a flow chart of an example of a method 1000 for removing a head assembly, which can include any of the heads and plugs discussed herein and others, from a surgically implanted stem, which can include any of the stems discussed herein and others. The head assembly can include a head, and, optionally, a plug. Prior to removal, the head can be attached by taper fit to a proximal portion of the stem. This method 1000 can avoid applying jarring forces or large torques to the implanted stem, and can therefore help prevent damage to the stem, the bone in which the stem is implanted, or the soft tissue surrounding the bone. The method 1000 of FIG. 10 is but one example; other suitable removal methods can also be used.

At 1002, method 1000 applies force distally to a non-peripheral portion of a proximal side of the head assembly. The proximal side of the head assembly can be configured to transmit an applied distal force to a proximal end of the stem.

In some examples, the applied distal and proximal forces sum to zero and are applied with a puller, such as 100 (FIG. 1). In some examples, the proximal side of the head assembly includes a plug disposed at the non-peripheral portion and proximal to the proximal end of the stem. For these examples, at 1004, the puller forces the plug into contact with the proximal end of the stem. In other examples, at the non-peripheral portion of the head assembly, the head is configured to deform in response to the applied distal force. For these examples, at 1006, after the non-peripheral portion of the head deforms, the puller forces the deformed non-peripheral portion of the head into contact with the proximal end of the stem. In still other examples, at the non-peripheral portion of the head assembly, the head is configured to break in response to the applied distal force. For these examples, at 1008, after the non-peripheral portion of the head breaks, the puller either forces the broken non-peripheral portion of the head into contact with the proximal end of the stem or directly contacts the proximal end of the stem.

At 1010, and simultaneously with 1002, method 1000 applies force proximally to a plurality of recessed portions on a distal side of the head. The recessed portions can be spaced apart around a circumference of the distal side. In some examples, the recessed portions are recessed by an amount greater than or equal to a thickness of an arm of the puller. In some examples, the recessed portions extend to an outer edge of the distal side of the head. In some examples, the distal side of the head includes two diametrically-opposed recessed portions thereon.

At 1012, method 1000 can optionally simultaneously increase the applied distal and proximal forces until the taper fit yields. At 1014, when the taper fit yields, the head assembly detaches from the implanted stem. The puller and head assembly can then be removed from the implanted stem. The practitioner can install a new head assembly onto the implanted stem, as needed.

Figure 11:
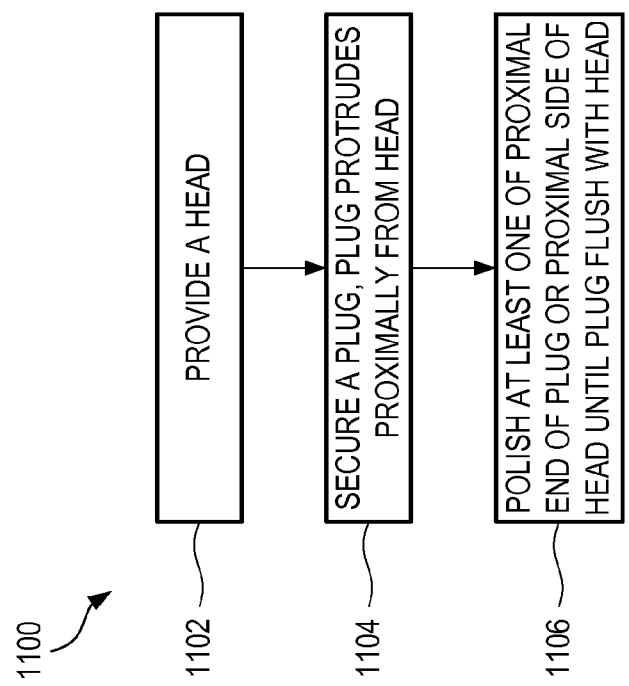
FIG. 11 is a flow chart of an example of a method for fabricating a head assembly for an artificial joint.

FIG. 11 is a flow chart of an example of a method 1100 for fabricating a head assembly, such as any of the head assemblies discussed herein and others, for an artificial joint. The method 1100 of FIG. 11 is but one example; other suitable fabricating methods can also be used.

At 1102, method 1100 provides a head having a proximal side and having an aperture extending through the proximal side. Suitable heads can include those discussed herein and others.

At 1104, method 1100 secures a plug within a proximal portion of the aperture. Suitable plugs can include those discussed herein and others. The secured plug can protrude proximally beyond the proximal side of the head.

At 1106, method 1100 removes material from at least one of a proximal end of the plug or the proximal side of the head until the proximal end of the plug is flush with the proximal side of the head. In some examples, the material can be removed by polishing, grinding, etching, and/or chemical processes that can controllably remove material from the proximal end of the plug.

In some examples, the head has a distal side opposite the proximal side, the distal side including a plurality of recessed portions thereon, the recessed portions being spaced apart around a circumference of the distal side. In some examples, the head has an internal wall that defines the aperture, the aperture extending from the proximal side to the distal side, the internal wall having a distal portion shaped to form a taper fit with a proximal portion of a stem.

The following non-limiting list of examples can further illustrate the present head assembly for an artificial joint, method for removing a head assembly from a surgically implanted stem, and method for fabricating a head assembly for an artificial joint.

In Example 1, a head assembly for an artificial joint can include a head having a proximal side, the head having a distal side opposite the proximal side, the distal side including a plurality of recessed portions thereon, the recessed portions being spaced apart around a circumference of the distal side, the head having an internal wall that defines an aperture extending from the proximal side to the distal side, the internal wall having a distal portion shaped to form a taper fit with a proximal portion of a stem; and a plug disposed in a proximal portion of the aperture, the plug having a proximal side flush with the proximal side of the head to form a continuous articular surface with the proximal side of the head.

In Example 2, the head assembly of Example 1 can optionally be configured such that the internal wall has a proximal portion shaped that is tapered inward.

In Example 3, the head assembly of Example 2 can optionally be configured such that the plug and aperture are centered, with respect to a longitudinal axis of the head.

In Example 4, the head assembly of Example 2 can optionally be configured such that the plug and aperture are decentered, with respect to a longitudinal axis of the head.

In Example 5, the head assembly of Example 4 can optionally be configured such that the longitudinal axis of the head intersects the plug and the aperture.

In Example 6, the head assembly of any one of Examples 1-5 can optionally be configured such that the distal side of the head includes two diametrically opposed recessed portions.

In Example 7, the head assembly of any one of Examples 1-6 can optionally be configured such that the recessed portions extend to an outer edge of the distal side of the head.

In Example 8, the head assembly of any one of Examples 1-7 can optionally be configured such that the proximal side of the head is convex.

In Example 9, a method for removing a head assembly from a surgically implanted stem, the head assembly including a head attached by taper fit to a proximal portion of the stem, the method can include simultaneously: applying force distally to a non-peripheral portion of a proximal side of the head assembly, the proximal side of the head assembly being configured to transmit an applied distal force to a proximal end of the stem; and applying force proximally to a plurality of recessed portions on a distal side of the head, the recessed portions being spaced apart around a circumference of the distal side.

In Example 10, the method of Example 9 can optionally further include simultaneously increasing the applied distal and proximal forces until the taper fit yields.

In Example 11, the method of Example 10 can optionally be configured such that the applied distal and proximal forces sum to zero and are applied with a puller.

In Example 12, the method of Example 11 can optionally be configured such that the recessed portions are recessed by an amount greater than or equal to a thickness of an arm of the puller.

In Example 13, the method of any one of Examples 11-12 can optionally be configured such that the recessed portions extend to an outer edge of the distal side of the head.

In Example 14, the method of any one of Examples 11-13 can optionally be configured such that the distal side of the head includes two diametrically-opposed recessed portions thereon.

In Example 15, the method of any one of Examples 11-14 can optionally be configured such that the proximal side of the head assembly includes a plug disposed at the non-peripheral portion and proximal to the proximal end of the stem; and the puller forces the plug into contact with the proximal end of the stem.

In Example 16, the method of any one of Examples 11-14 can optionally be configured such that at the non-peripheral portion of the head assembly, the head is configured to deform in response to the applied distal force; and after the non-peripheral portion of the head deforms, the puller forces the deformed non-peripheral portion of the head into contact with the proximal end of the stem.

In Example 17, the method of any one of Examples 11-14 can optionally be configured such that at the non-peripheral portion of the head assembly, the head is configured to break in response to the applied distal force; and after the non-peripheral portion of the head breaks, the puller either forces the broken non-peripheral portion of the head into contact with the proximal end of the stem or directly contacts the proximal end of the stem.

In Example 18, a method for fabricating a head assembly for an artificial joint can include providing a head having a proximal side and having an aperture extending through the proximal side; securing a plug within a proximal portion of the aperture, the secured plug protruding proximally beyond the proximal side of the head; and removing material from at least one of a proximal end of the plug or the proximal side of the head until the proximal end of the plug is flush with the proximal side of the head.

In Example 19, the method of Example 18 can optionally be configured such that the head has a distal side opposite the proximal side, the distal side including a plurality of recessed portions thereon, the recessed portions being spaced apart around a circumference of the distal side.

In Example 20, the method of Example 19 can optionally be configured such that the head has an internal wall that defines the aperture, the aperture extending from the proximal side to the distal side, the internal wall having a distal portion shaped to form a taper fit with a proximal portion of a stem.

In Example 21, the head assembly or method of any one or any combination of Examples 1-20 can optionally be configured such that all elements, operations, or other options recited are available to use or select from.

The above Detailed Description includes references to the accompanying drawings, which form a part of the Detailed Description. The drawings show, by way of illustration, specific embodiments in which the invention can be practiced. These embodiments are also referred to herein as "examples." Such examples can include elements in addition to those shown or described. However, the inventors also contemplate examples in which only those elements shown or described are provided. Moreover, the inventors also contemplate examples using any combination or permutation of those elements shown or described (or one or more aspects thereof), either with respect to a particular example (or one or more aspects thereof), or with respect to other examples (or one or more aspects thereof) shown or described herein. In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, kit, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects. The above description is intended to be illustrative, and not restrictive. For example, the above-described examples (or one or more aspects thereof) can be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A head assembly for an artificial joint, comprising:
a head having a proximal surface,
the head having a distal surface opposite the proximal surface, the distal surface including a plurality of recessed portions thereon, the recessed portions being spaced apart around a circumference of the distal surface,
the head having an internal wall that defines an aperture extending from the proximal surface to the distal surface, the internal wall having a distal portion shaped to form a taper fit with a proximal portion of a stem; and
a plug disposed in a proximal portion of the aperture, the plug having a proximal surface flush with the proximal surface of the head to form a continuous convex articular surface with the proximal surface of the head.

2. The head assembly of claim 1, wherein the internal wall has a proximal portion shaped that is tapered inward.

3. The head assembly of claim 2, wherein the plug and aperture are decentered, with respect to a longitudinal axis of the head.

4. The head assembly of claim 3, wherein the longitudinal axis of the head intersects the plug and the aperture.

5. The head assembly of claim 2, wherein the plug and aperture are centered, with respect to a longitudinal axis of the head.

6. The head assembly of claim 1, wherein the distal surface of the head includes two diametrically opposed recessed portions.

7. The head assembly of claim 1, wherein the recessed portions extend to an outer edge of the distal surface of the head.

8. Ahead assembly for an artificial joint, comprising:
a head having a proximal side,
the head having a distal side opposite the proximal side, the distal side including a plurality of recessed portions thereon, the recessed portions being spaced apart around a circumference of the distal side,
the head having an internal wall that defines an aperture extending from the proximal side to the distal side, the internal wall having a distal portion shaped to form a taper fit with a proximal portion of a stem, the internal wall having a proximal portion shaped that is tapered inward; and
a plug disposed in a proximal portion of the aperture, the plug having a proximal side flush with the proximal side of the head to form a continuous articular surface with the proximal side of the head,
wherein the plug and aperture are decentered, with respect to a longitudinal axis of the head.

9. The head assembly of claim 8, wherein the longitudinal axis of the head intersects the plug and the aperture.

* * * * *